United States Patent [19]
Moore et al.

[11] Patent Number: 5,993,387
[45] Date of Patent: Nov. 30, 1999

[54] COMPUTER-BASED MIXED-USE REGISTRY OF PLACENTAL AND UMBILICAL CORD STEM CELLS

[75] Inventors: Thomas Eldon Moore, Los Altos Hills, Calif.; David Thomas Harris, Tucson, Ariz.; Jesse O. Kramer, San Francisco, Calif.

[73] Assignee: Core Blood Registry, Inc., San Bruno, Calif.

[21] Appl. No.: 08/910,996

[22] Filed: Aug. 14, 1997

[51] Int. Cl.$^6$ ........................................................ A61B 5/00
[52] U.S. Cl. ............................... 600/300; 705/2; 707/104; 707/200; 435/2
[58] Field of Search ..................................... 600/300, 301; 62/266, 336, 337; 705/2, 3; 707/100, 104, 200; 435/2

[56] References Cited

U.S. PATENT DOCUMENTS 5,125,240   6/1992   Knippscheer et al. ..................... 62/266

OTHER PUBLICATIONS

J. Stephenson, Terms of Engraftment: Umbilical Cord Blood Transplants, JAMA, Jun. 21, 1995, pp. 1813–1815.

John E. Wagner et al., Allogeneic sibling umbilical–cord blood transplantation in children with malignant and non–malignant disease, The Lancet, Jul. 22, 1995, pp. 214–219.

Clare Thompson, Umbilical Cords: Turning Garbage Into Clinical Gold, Biomedical Research, May 12, 1995, pp. 805–806.

Jeremy Sugarman, MD et al., Ethical Aspects of Banking Placental Blood for Transplantation, JAMA, Dec. 13, 1995, pp. 1783–1785.

Dr. David T. Harris, Cord Blood and Its Potential Clinical Applications, Clinical Research News for Arizona Physicians, Dec. 1995, vol. 6, No. 12.

Julie Carrick Dalton, New Hope from a New Life, Dallas Child, Aug. 1995, pp. 21–24.

*Primary Examiner*—Ruth S. Smith
*Attorney, Agent, or Firm*—Pillsbury Madison & Sutro LLP

[57] ABSTRACT

A computer-based mixed-use cord stem cells registry system, method and device are provided for developing and maintaining a mixed-used bank of placental and umbilical cord stem cells and for the resultant bank. The cord stem cells, or a fraction thereof, is stored in a bank for the potential use of the donor and potentially the actual family of the donor child or from an unrelated person for whom the cord stem cells are a match. The system makes the cord stem cells available to the family until the blood sample is found to match a non-family member in need of the cord stem cells. At this time the family is given an option of keeping the sample for themselves or of providing it to the non-family member along with current information on the donor family.

29 Claims, 3 Drawing Sheets

COMPUTER-BASED MIXED-USE REGISTRY OF PLACENTAL AND UMBILICAL CORD STEM CELLS

BACKGROUND OF THE INVENTION

1. Reservation of Copyright

The disclosure of this patent document contains material which is subject to copyright protection. The copyright owner has no objection to the facsimile reproduction by anyone of the patent document or the patent disclosure, as it appears in the U.S. Patent and Trademark Office patent files or records, but otherwise reserves all copyrights whatsoever.

2. Field of Invention

This invention relates to a system, method and apparatus for maintaining a cord stem cell registry. More particularly, this invention relates to a method and system for a mixed-use bank of placental and umbilical cord stem cells.

3. Description of Background Information

Placental and umbilical cord stem cells (hereinafter "cord stem cells"), harvested from the placenta and umbilical cord of newborn infants, has been found to contain a high concentration of hematopoietic stem cells which create the blood and immune systems. These stem cells have been successfully used in transplant settings for a wide variety of diseases including certain cancers such as leukemia, blood anemias and genetic disorders.

Medical applications of cord stem cells are becoming well-known in and out of the medical community. For general discussions as well as particular applications of cord stem cells, see, for example, J. Stephenson, "Terms of Engraftment: Umbilical Cord Blood Transplants Arouse Enthusiasm," 273 *JAMA* 23, Jun. 21, 1995; John E. Wagner et al, "Allogeneic sibling umbilical-cord-blood transplantation in children with malignant and non-malignant disease," 346 *The Lancet* 8969, pp. 214–219, Jul. 1995; and Clare Thompson, "Umbilical Cords: Turning Garbage Into Clinical Gold," 268 *Science* 805, May 12, 1995.

As a result of the successful clinical experiences and the large number of people who have benefitted from the medical uses of cord stem cells to date (or who will benefit from cord stem cells uses in the future), several cord stem cell banks have been established.

To date there are two kinds of cord stem cell banks. The first kind of cord stem cell banks, family banks, store harvested cord stem cells for a donor's family and provide a sample of the donated cord stem cells back to the donor family if needed. Public banks have been established to provide typed, anonymous samples to the general public based on genetic matching with needy potential recipients. A general discussion of various ethical issues relating to cord-blood banks is provided in Jeremy Sugarman et al, "Ethical Aspects of Banking Placental Blood for Transplantation," 274 *JAMA* 22, pp. 1783–85, Dec., 13, 1995.

While there are ethical advantages, possibly even requirements, on anonymity of cord stem cell samples, there are some definite disadvantages. First, there is always the possibility that the donor family will need to use the sample, and anonymity makes such a use more difficult. Further, even if a cord stem cell sample is used by an individual not related to the donor family, there may still be advantages in being able to find out more information about the donor and/or the donor's family. For example, the ability to find out information about the donor (obtain a "then current look" in the future at the time of use to the donor) can reduce the risk of transmitting acquired or genetic diseases on transplant of the cord stem cells years later.

The so-called public cord stem cell banks generally allow for an initial non-anonymous period of cord stem cell sample storage, say, six months, after which the samples are anonymized in order to prevent future ethical conflicts. Once a sample is anonymized, it is not possible for a user of a public cord stem cell bank to look back to the donor or the donor's family.

No mixed-use cord stem cell banks have yet been established. That is, no cord stem cell banks have been established which allow for both typed, anonymous samples and for exclusive family use and retention of the cord stem cell samples.

SUMMARY OF THE INVENTION

It is desirable to provide a cord stem cell bank which includes the advantages of both family and public cord stem cell banks. That is, it is desirable to provide a cord stem cell bank which provides for donor and donor family use, if needed, while also providing anonymity and then-current-look to the donor family in the future, at the time when the sample is used.

It is therefore an object of this invention to provide a mixed-use cord stem cell bank.

It is another object of this invention to provide better data and thus allow physicians to have better selection criteria and thereby better clinical outcomes.

Accordingly, this invention provides a device, method and system for maintaining a computer-based mixed-use cord stem cells registry.

The invention provides for creating a new donor record for a potential donor in a cord stem cells database of the registry; storing donor identification information in the new record; storing sample identification information in the new record; storing type information about a collected sample in the new record; storing an availability indication with the new record to indicate the potential availability of the cord stem cell sample; and storing the collected cord stem cell sample in a bank such that the sample can be obtained from the bank using the stored sample identification information.

In some embodiments, the invention provides for modifying the availability indication for a particular donor record.

In some embodiments the invention provides for updating the type information for a particular donor record.

The invention further provides, in some embodiments, for obtaining recipient type information for a possible cord stem cells recipient; and for searching the database to determine if there is a sample which matches the recipient type information.

In preferred embodiments the searching is based on at least some information in the type information field of the records in the database.

In preferred embodiments, only records marked as available are searched.

In some cases, after an appropriate match is found, modifying the availability indication for the matching record.

In some cases, after an appropriate match is found, updating the type information for a particular donor record.

The type information includes at least one of genetic type information, family medical history and information relating to ethnic and geographic origin of the donor. Other donor information such as donor phenotype may also be included.

The mixed-use cord stem cell bank of the present invention has the advantages of both a family and a public bank.

BRIEF DESCRIPTION OF THE DRAWINGS

The above and other objects, features, and advantages of the present invention are further described in the detailed description which follows, with reference to the drawings by way of non-limiting exemplary embodiments of the present invention, wherein like reference numerals represent similar parts of the present invention throughout the several views and wherein.

DETAILED DESCRIPTION OF THE PRESENTLY PREFERRED EXEMPLARY EMBODIMENTS

Figure 1:
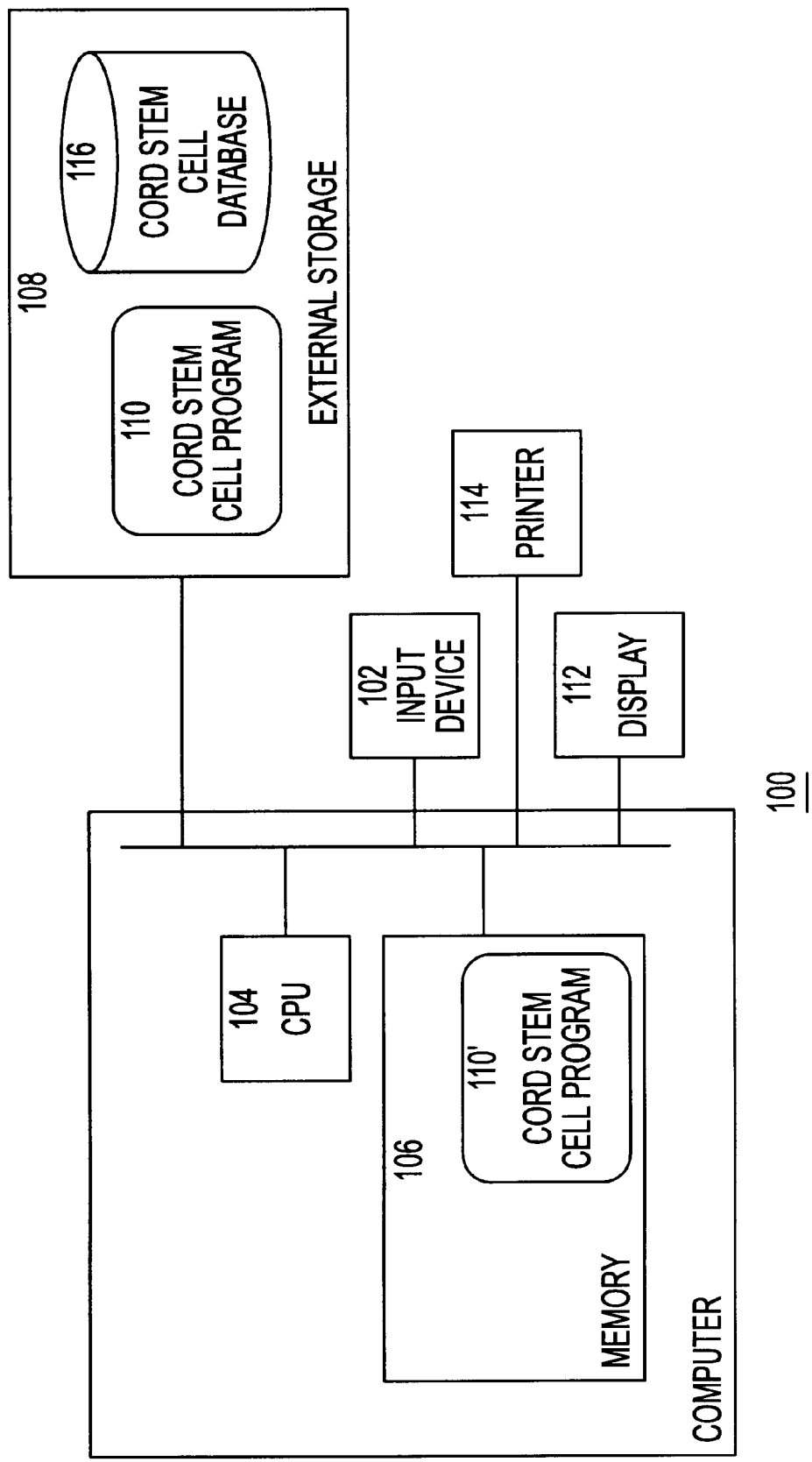
FIG. 1 depicts a typical computer system on which the system of this invention operates.

This invention operates on a typical computer system 100 such as shown in FIG. 1. The computer system 100 includes various input devices 102 such as a keyboard. The computer system 100 also includes a processor such as CPU 104 and internal memory 106. The processor 104 may be a special purpose processor with database processing capabilities or it may be a general purpose processor. The memory 106 may comprise various types of memory, including RAM, ROM, and the like. The computer system 100 also includes external storage 108 which includes devices such as disks, CD ROMs, ASICs, external RAM, external ROM and the like.

The present invention can be implemented as part of the processor 104 or as a program residing in memory 106 (cord stem cells program 110') (and external storage 108 (cord stem cells program 110)) and running on processor 104, or as a combination of program and specialized hardware. When in memory 106 and/or external storage 108, the program 110, 110' can be in a RAM, a ROM, an internal or external disk, a CD ROM, an ASIC or the like. In general, when implemented as a program or in part as a program, the program can be encoded on any computer-readable medium or combination of computer-readable media, including but not limited to a RAM, a ROM, a disk, an ASIC, a PROM and the like.

The computer system 100 also includes a display 112 and, optionally, an output device such as a printer 114.

The computer system 100 can run any operating system. The cord stem cells computer program 110 (110') can be implemented in any computer programming language or combination of computer programming languages, although preferably it is implemented, at least in part, in a language which is suitable for database access and manipulation.

The mixed-use cord stem cell bank according to the present invention uses a cord stem cells database 116, typically stored in external storage 108.

Figure 2:
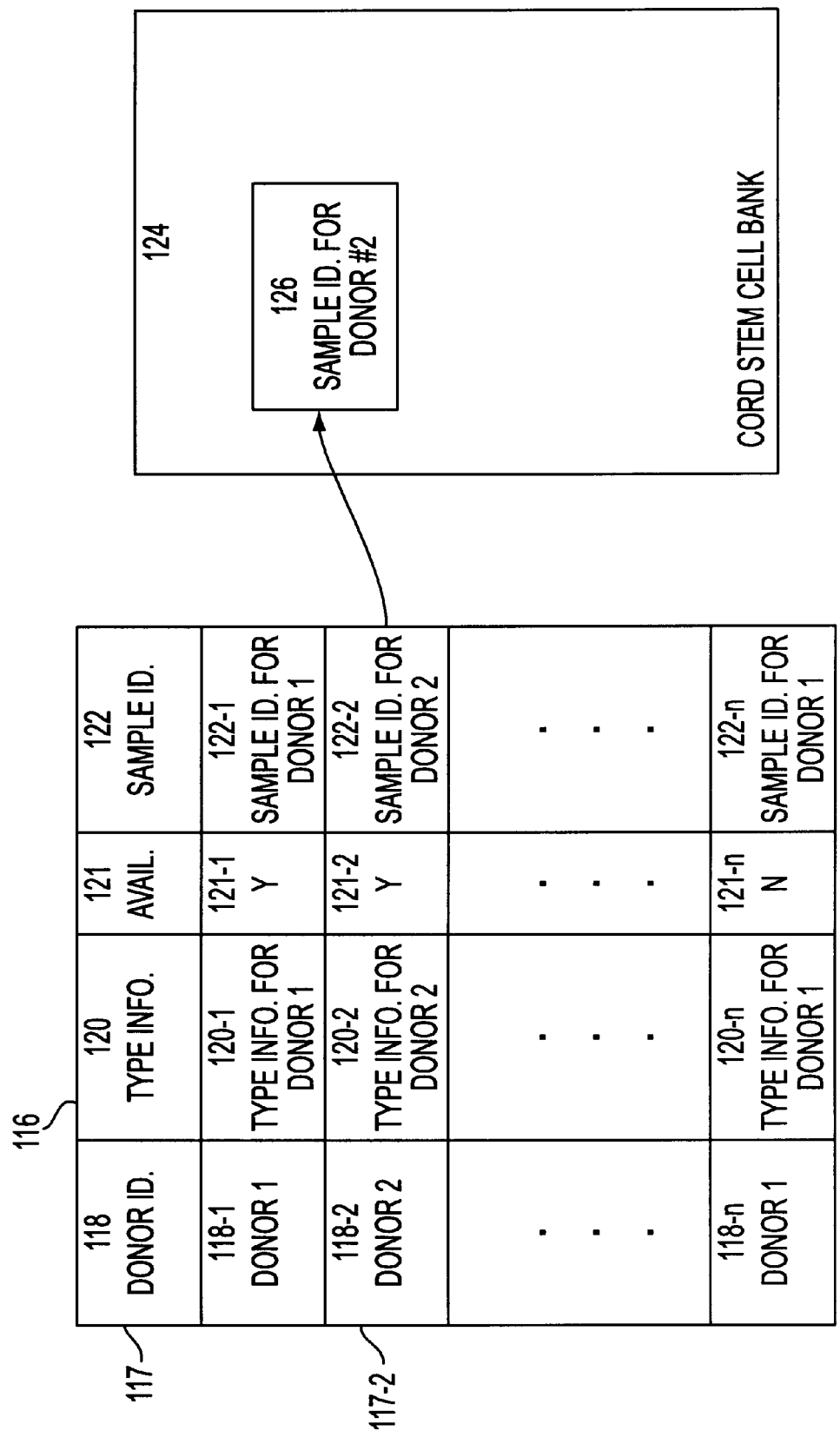
FIG. 2 shows the logical structure of the cord stem cells database according to this invention.
Figure 3:
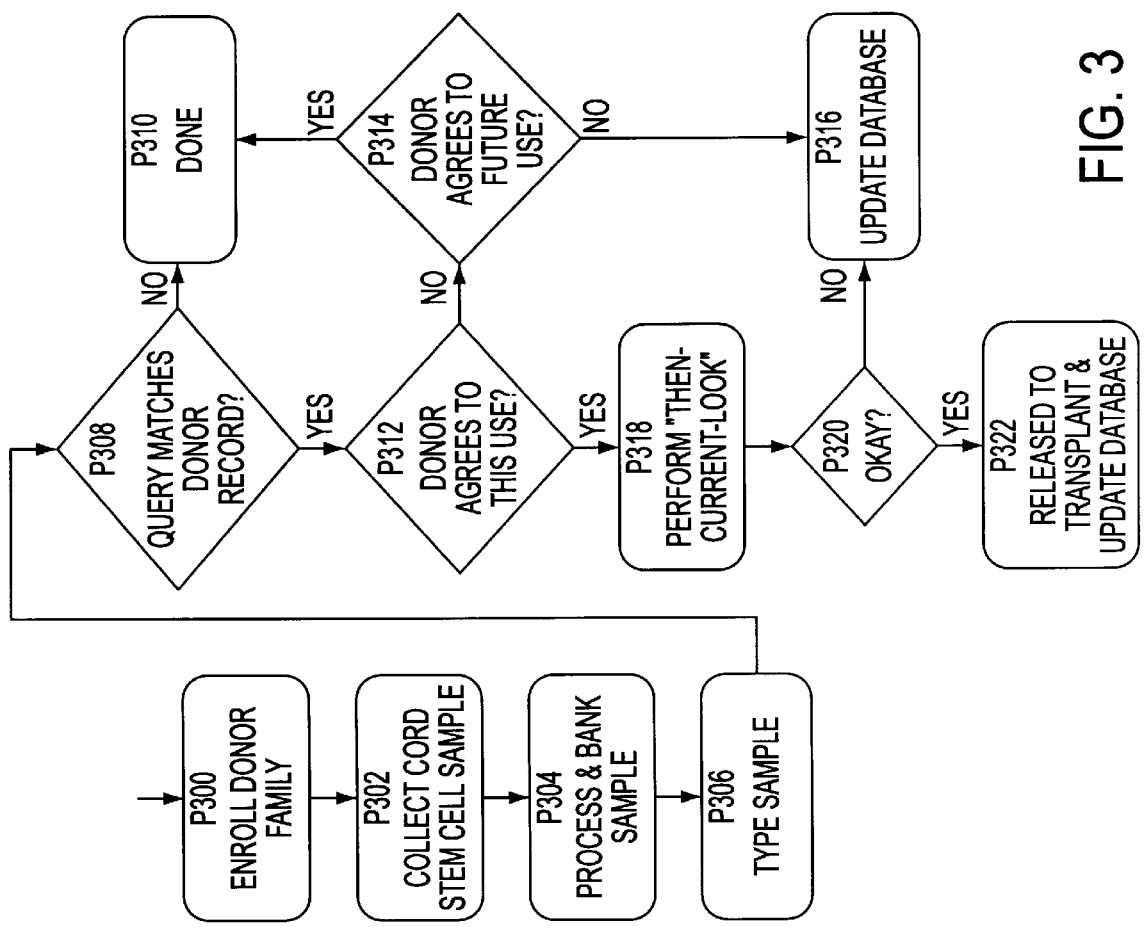
FIG. 3 shows a flow diagram for setting up a database entry in the cord stem cells database of FIG. 2.

The logical structure of the cord stem cells database 116 is shown in FIG. 2 which illustrates that each record 117 of the database 116 has three main fields, each of which can have numerous sub-fields. As shown in FIG. 3, for each cord stem cell sample 126 in the cord stem cell bank, there is a database record 117 with three main database fields. These three fields are the donor identifier field 118, the sample type information field 120 and the sample identifier field 122.

Preferably the database 116 can be searched on at least any of the three fields 118, 120, 122, and on sub-fields of those fields.

Preferably the sample type information field 120 has genetic and other searchable type information about the cord stem cell sample for the donor associated with the record. In some preferred embodiments, the field 120 can also contain information about other family members. For example, it may be useful to know of any known disease histories of the donor's family. The type information 120 can also include such information as donor's family medical history and information relating to ethnic and geographic origin of the donor. Other donor information such as donor phenotype may also be included in the type information 120.

Each database record 117 also has a field 121 indicating whether the sample 126 associated with the record 117 is available for public use.

Thus, as shown in FIG. 2, the sample from donor #2 126, has a record 117-2 in the database 116. The database record 117-2 has a donor identity field 118-2 which identifies donor #2. The sample type information field 120-2 has genetic and other searchable type information about the cord stem cell sample 126. The sample identifier field 122-2 identifies the actual sample 126 in such a way that the sample can be physically located should it be needed. The "available" field 121-2 for the sample 126 is set to "Yes", indicating that the sample is available to the public.

The single database structure in FIG. 2 is merely provided as a logical description of the database. In preferred embodiments the various sub-relationships might be maintained as separate databases. Further, for privacy reasons, not all users of the database 116 are provided with access to all the fields. Therefore, for example, only some users can search based on the type information field 120 and only restricted access is provided to searches on the sample identifier field 122. In this manner, unauthorized matching of type information with donors is prevented.

Operation

There are two aspects to the operation of the mixed-use cord stem cell bank according to the present invention. The first aspect relates to initial storing of data in the cord stem cell bank, and the second relates to subsequent searching and accessing of the cord stem cell bank.

The first aspect, initial storing of data in the cord stem cell bank is described with reference to FIGS. 1–3.

Before a child is born, a family enrolls (at P300) with the bank and pays a fee for the collection and storage of the cord stem cells to be collected from their new-born. Upon enrollment, a database record 117 is created for the potential donor family in the cord stem cells database 116. Some of the information in the donor identity field 118 is provided (other information such as the sex of the donor infant may not yet be known upon enrollment).

At the time of enrollment, each potential donor is provided with a unique sample identifier which will become associated with their cord stem cell sample once it is collected. This unique sample identifier is associated with the specific donor in the cord stem cells database 116 by setting the value of the sample identifier field 122 for the record 117 for this particular donor.

Upon enrollment, the donor family can elect to make the sample available to the public for searching and possible use. If such an election is made, the "available" field 121 for this donor is set to "Yes", otherwise it is set to "No".

Thus, upon completion of enrollment (at P300), the potential donor has a partially complete database record 117 in the cord stem cells database 116. Some of the donor's identifying information (e.g., parents' names, address etc.) stored in the donor identity field 118 of the record 117, and a unique sample identifier is stored in the sample identifier field 122 of the record 117. The "available" field 121 of the record is also set to either "Yes" or "No".

Note that until the cord stem cell sample is actually collected and stored, this database record 117 remains incomplete. If, for some reason, the sample is not collected or cannot be added to the database, then this record can be deleted.

Note also that the donor identity will require more information than just one or more of the parents' names since a family may be donors for more than one child.

When the donor infant is born, the cord stem cell sample 126 is collected (at P302), and is processed and banked (at P304) in cord stem cell bank 124 using well-known and established procedures. Preferably the cord stem cell sample is cryogenically banked in a cryogenic tank which can be accessed at a later time, as needed.

The identity of the cord stem cell sample 126 in the cord stem cell bank 124 is the same (or can be determined from) the value stored in the associated sample identifier field 122 of the record 117 for that sample's donor. In this way, given a particular donor, the cord stem cells database 116 can be used to locate a cord stem cell sample 126 for a given donor.

The collected sample 126 is also genetically typed (at P306) to the extent that someone seeking a cord stem cell sample for a patient not related to the donor can determine the degree of genetic matching between the sample 126 and the intended patient. The genetic type information is stored in the type information field 120 of the record 117 for the sample's donor.

Preferably the genetic type information is stored in a manner which allows for searching and matching such information.

Note that at any time the donor (donor's family) can elect to change the "available" field 121 for their particular donation.

Also, preferably the donor will provide the cord stem cell bank with updated medical information relating to possible diseases which were unknown or undetectable at the time the cells were collected.

When a donor is sought for a particular party, the database 116 is searched for a donor matching the party. The search uses an appropriate matching algorithm based on the data in the type information 120 fields of available records. If no matching donor record 117 is found (at P308), the processing is complete (at P310). On the other hand, if a matching donor record is found (at P308), then it is ascertained whether or not the donor agrees to this use of the sample 126 (at P312). If the donor does not agree to this use, then it is ascertained whether or not the donor will agree to any future uses of this sample (at P314). If the donor might agree to future uses of the sample then processing is complete (at P310), otherwise the database is updated (at P316) to indicate that this sample is not available. That is, the availability field 121 of the matching donor's record 117 is set to "NO" to indicate unavailability of this donor's sample. This scenario can occur when a donor decides that a sample should no longer be available.

If the donor does agree to this use (at P312), then, if possible, more information is obtained (at P318) from or about the donor. This information could include information that was not available or ascertainable at the time the sample was made.

Based on the new information, the acceptability of the matching sample is re-evaluated (at P320). If the sample is unacceptable then the database is updated with the new information (at P316) and processing is done.

If the sample is acceptable then the sample is used and the database is updated to indicate this use (at P322).

Various incentives can be provided to encourage donors to update their records. For example, free or reduced rates for sample retention can be offered to donors who update their information.

The second aspect of using the cord stem cell bank according to the present invention is now described with reference to FIGS. 1 and 2.

When a party, usually a physician or a transplant organization, needs to find a cord stem cells match for a patient, first some appropriate genetic information is obtained from the patient. Then the cord stem cells database 116 is searched for available samples (based on the available field 121) using the type information for the donor field 120 to determine whether a suitable cord stem cell sample is present in the cord stem cell bank.

In some embodiments, even non-available samples (based on the available field 121) are searched, so that if an unavailable sample is found to match, the cord stem cell bank may still elect to contact the donor to determine if the sample continues to be unavailable.

If a potential match is found, the donor (or donor's family) is contacted and presented with three choices.

First, the donor may choose to keep the sample for themselves but to have the sample remain on the registry of available samples. That is, the sample can remain in the database 116 as a searchable and available sample.

Second, the donor can choose to keep the sample for themselves and to have the sample removed from the registry of available samples. That is, the sample no longer remains in the database 116 as a searchable and available sample. That is, the "available" field 121 for the sample is set to "No".

Third, the donor can choose to provide the matching sample to the potential patient. If the donor elects this third option, the donor may be asked to provide further blood, other medical tests and/or historic information, thereby allowing a more current evaluation of the match and sample donor attributes. Further, if the donor elects this third option, they may be refunded the fees paid to date and/or provided with some form of rebate based on the compatibility.

Knowing the identity of the donor allows the potential recipient to obtain updated and current information about the donor and the donor's current health. Some of this information may not have been medically available or feasible at the time the cell donation was made.

Accordingly, the cord stem cell bank of the present invention provides a donor's family with the option of retaining the cord stem cell sample, if needed by the family, while at the same time making it potentially available those who may need it. The decision as to whether or not to donate the sample, if it is needed, can thus be deferred or delayed.

The financial opportunity provided to customers of a mixed-use cord stem cell bank represents an insurance instrument since the donor family can get back some or all of the fees paid to store the sample should they elect to provide the sample to another party.

Although described with reference to a particular system, the present invention operates on any computer system and can be implemented in software, hardware or any combination thereof. When implemented fully or partially in software, the invention can reside, permanently or temporarily, on any memory or storage medium, including but not limited to a RAM, a ROM, a disk, an ASIC, a PROM and the like.

Thus, a computer-based mixed-use cord stem cells registry is provided. One skilled in the art will appreciate that the present invention can be practiced by other than the described embodiments, which are presented for purposes of illustration and not limitation, and the present invention is limited only by the claims that follow.

What is claimed:

1. A method of maintaining a computer-based mixed-use cord stem cells registry, the method comprising:
   creating a new donor record for a potential donor in a cord stem cells database of the registry;
   storing donor identification information in the new record;
   storing sample identification information in the new record;
   collecting a cord stem cell sample from the donor;
   typing the collected cord stem cell sample and storing type information about the sample type in the new record;
   storing an availability indication with the new record to indicate whether the cord stem cell sample is available for public use;
   storing the collected cord stem cell sample in a bank such that the sample can be obtained from the bank using the stored sample identification information; and
   modifying the availability indication for a particular donor record when the record's availability for public use changes.

2. A method as in claim 1 further comprising:
   updating the type information for a particular donor record.

3. A method as in claim 2 wherein the type information is updated with information not known when the cord stem cell sample was typed.

4. A method as in claim 1 further comprising:
   obtaining recipient type information for a possible cord stem cells recipient; and
   searching the database to determine if there is a sample which matches the recipient type information.

5. A method as in claim 4 wherein the searching is based on at least some information in the type information field of the records in the database.

6. A method as in claim 4 wherein only records marked as available for public use are searched.

7. A method as in claim 4 further comprising, after an appropriate match is found, modifying the availability indication for the matching record.

8. A method as in claim 4 further comprising, after an appropriate match is found, updating the type information for a particular donor record.

9. A method as in claim 1 wherein the type information includes at least one of genetic type information and family medical history.

10. A computer-readable medium or combination of computer-readable media, containing a program for maintaining a computer-based mixed-use cord stem cells registry, the program comprising code to effect:
    creating a new donor record for a potential donor in a cord stem cells database of the registry;
    storing donor identification information in the new record;
    storing sample identification information in the new record;
    storing type information about a collected cord stem cell sample type in the new record; and
    storing an availability indication with the new record to indicate whether the cord stem cell sample is available for public use.

11. A computer-readable medium or combination of computer-readable media as in claim 10 wherein the program further comprises code to effect:
    modifying the availability indication for a particular donor record when that record's availability for public use changes.

12. A computer-readable medium or combination of computer-readable media as in claim 11 wherein the program further comprises code to effect:
    updating the type information for a particular donor record.

13. A medium or media as in claim 12 wherein the type information is updated with information not known when the cord stem cell sample was typed.

14. A medium or media as in any one of claims 10–13 wherein the medium or media comprise but are not limited to a RAM, a ROM, a disk, an ASIC, and a PROM.

15. A medium or media as in claim 11 wherein the program further comprises code to effect:
    obtaining recipient type information for a possible cord stem cells recipient; and
    searching the database to determine if there is a sample which matches the recipient type information.

16. A medium or media as in claim 15 wherein the searching is based on at least some information in the type information field of the records in the database.

17. A medium or media as in claim 15 wherein only records marked as available for public use are searched.

18. A medium or media as in claim 15 further comprising code to effect, after an appropriate match is found, modifying the availability indication for the matching record.

19. A medium or media as in claim 15 further comprising code to effect, after an appropriate match is found, updating the type information for a particular donor record.

20. A device for maintaining a computer-based mixed-use cord stem cells registry, the device comprising:
    means for creating a new donor record for a potential donor in a cord stem cells database of the registry;
    means for storing donor identification information in the new record;
    means for storing sample identification information in the new record;
    means for storing type information about a collected sample in the new record;
    means for storing an availability indication with the new record to indicate whether the cord stem cell sample is available for public use; and
    means for storing the collected cord stem cell sample in a bank such that the sample can be obtained from the bank using the stored sample identification information.

21. A device as in claim 20 further comprising:
    means for modifying the availability indication for a particular donor record when the record's availability for public use changes.

22. A device as in claim 20 further comprising:
    means for updating the type information for a particular donor record.

23. A device as in claim 22 wherein the type information includes at least one of genetic type information and family medical history.

24. A device as in claim 22 wherein the type information is updated with information not known when the cord stem cell sample was typed.

25. A device as in claim 20 futher comprising:
    means for obtaining recipient type information for a possible cord stem cells recipient; and
    means for searching the database to determine if there is a sample which matches the recipient type information.

26. A device as in claim 25 wherein the searching is based on at least some information in the type information field of the records in the database.

27. A device as in claim 25 wherein only records marked as available for public use are searched.

28. A device as in claim 25 further comprising:
    modifying means for, after an appropriate match is found, modifying the availability indication for the matching record.

29. A device as in claim 25 further comprising:
    updating means for, after an appropriate match is found, updating the type information for a particular donor record.

* * * * *

UNITED STATES PATENT AND TRADEMARK OFFICE
CERTIFICATE OF CORRECTION

| | | |
|---|---|---|
| PATENT NO. | : 5,993,387 | Page 1 of 1 |
| APPLICATION NO. | : 08/910996 | |
| DATED | : November 30, 1999 | |
| INVENTOR(S) | : Thomas E. Moore et al. | |

It is certified that error appears in the above-identified patent and that said Letters Patent is hereby corrected as shown below:

On the Title page Item [73] Assignee:
Please replace "Core Blood Registry, Inc." with "Cord Blood Registry, Inc."

Signed and Sealed this
Twenty-third Day of August, 2011

David J. Kappos
*Director of the United States Patent and Trademark Office*